United States Patent
Garcia (10) Patent No.: US 11,638,808 B2
(45) Date of Patent: May 2, 2023

(54) NEOVAGINAL AND VAGINAL HEALTH DEVICES

(71) Applicant: The Regents of the University of California, Oakland, CA (US)

(72) Inventor: Maurice Marcel Garcia, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 956 days.

(21) Appl. No.: 16/349,835

(22) PCT Filed: Nov. 14, 2017

(86) PCT No.: PCT/US2017/061566
§ 371 (c)(1),
(2) Date: May 14, 2019

(87) PCT Pub. No.: WO2018/090014
PCT Pub. Date: May 17, 2018

(65) Prior Publication Data
US 2020/0054868 A1    Feb. 20, 2020

Related U.S. Application Data (60) Provisional application No. 62/421,492, filed on Nov. 14, 2016.

(51) Int. Cl.
*A61M 29/00* (2006.01)
*A61B 17/43* (2006.01)
(Continued)

(52) U.S. Cl.
CPC .............. *A61M 29/00* (2013.01); *A61B 17/43* (2013.01); *A61F 5/442* (2013.01); *A61H 19/44* (2013.01);
(Continued)

(58) Field of Classification Search
CPC .... A61M 29/00; A61M 3/0279; A61M 29/02; A61M 3/02; A61B 17/43; A61F 5/442;
(Continued)

(56) References Cited

U.S. PATENT DOCUMENTS 3,799,170 A    3/1974    Walsh et al.
5,681,340 A    10/1997   Veronikis
(Continued)

FOREIGN PATENT DOCUMENTS

KR    20-1998-061965 U    11/1998
KR    10-2007-0005863 A    1/2007

OTHER PUBLICATIONS

Unger, C.A., et al., "Construction of the Neovagina," Chapter 18, Female Pelvic Surgery, First online published on Sep. 18, 2014. pp. 267-290, DOI: 10/1007/978-1-4939-1504-0_18. See McIndoe Procedure on p. 270, 271; figures 18.2.

(Continued)

*Primary Examiner* — John P Lacyk
(74) *Attorney, Agent, or Firm* — Marshall, Gerstein & Borun LLP (57) ABSTRACT

The scope of the invention encompasses novel, multifunctional tools for maintaining the neovagina. The tools comprise novel dilator shapes that conform the anatomical pathway of the neovagina. The tools may further include a douching function for the effective and thorough washing of the neovagina, which is not achieved with standard douching devices. The tools may also comprise a measurement function for medical evaluation of the neovagina and to aid in proper dilation. Also presented herein are novel devices for delivery of agents to the natal vagina, including insemination devices.

21 Claims, 5 Drawing Sheets

(51) Int. Cl.
*A61F 5/442* (2006.01)
*A61H 19/00* (2006.01)
*A61M 3/02* (2006.01)
*A61B 90/00* (2016.01)

(52) U.S. Cl.
CPC ..... *A61M 3/0279* (2013.01); *A61B 2090/062* (2016.02); *A61H 2201/1253* (2013.01); *A61M 2210/1475* (2013.01)

(58) Field of Classification Search
CPC ........... A61F 2/00; A61H 19/44; A61D 19/00; A61D 19/02; A61D 19/027
See application file for complete search history.

(56) References Cited

U.S. PATENT DOCUMENTS

| | | | | |
|---|---|---|---|---|
| 6,224,580 B1 * | 5/2001 | Christensen | .......... | A61M 29/00 604/275 |
| 2007/0043388 A1 * | 2/2007 | Greenwood | .......... | A61M 29/00 606/193 |

OTHER PUBLICATIONS

International Search Report for PCT/US17/061566, KIPO, dated Feb. 21, 2018. See pp. 8-13.

\* cited by examiner

NEOVAGINAL AND VAGINAL HEALTH DEVICES

CROSS-REFERENCE TO RELATED APPLICATIONS

This application is a 35 USC § 371 national stage application of, and claims priority to International Application No. PCT/US2017/61566, entitled "Neovaginal and Vaginal Health Devices," filed on Nov. 14, 2017, which claims priority to U.S. Provisional Application No. 62/421,492, entitled "Integrated Neovaginal Dilator, Depth Measurement, and Cleansing Device," filed on Nov. 14, 2016, each of which is incorporated by reference herein in its entirety.

STATEMENT REGARDING FEDERALLY SPONSORED RESEARCH OR DEVELOPMENT

Not applicable.

BACKGROUND AND SUMMARY OF THE INVENTION

The various embodiments of the invention are related to devices which can be used to maintain the health of the vagina or neovagina.

Regarding the neovagina, this is a surgically-created vagina. Neovaginas are found in natal women that have undergone vaginoplasty to address vaginal damage resulting from trauma, surgery, stenosis, congenital deformities, or other causes. The neovagina is also found in transgender individuals that have undergone male-to-female genital gender affirming surgery.

Following surgical creation of a neovagina, the patient must perform two "maintenance" tasks in order to maintain the patency and health of the neovagina. First, the patient must dilate the neo-vagina in order to maintain its patency, or state of openness and unobstruction. A neovagina, like many channels in the body is only a potential space, and if not filled, will collapse. If the neovagina is not regularly dilated, it can potentially undergo stricture, i.e. narrowing/closure, due to the formation of scar tissue. Dilation is performed by inserting a tubular dilator into the neo-vagina for a period of time (for example 20 minutes, one to three times per day) to stretch and maintain the patency of the channel.

The second maintenance task that persons with neovaginas must perform is douching, in order to maintain the health of the skin from which it is formed (which is non-absorbing of liquid) or bowel tissue, if bowel is used to create the neovagina (which produces mucus indefinitely) which lines the inner lumen of the neo-vagina space. Douching products on the market are designed for natal vaginas or the rectum and are not of optimal length, shape or design for douching of the neovagina. Specifically, the insertable nozzle of currently available douches is shorter than is necessary to ensure that irrigant is forced under pressure from the proximal portion of the neovagina into the deepest portion thereof. The shape of commonly available douches is not ideal for smooth insertion (i.e. with minimal resistance) into a neovagina. Lastly, currently available douches do not have the irrigation hole at the very tip of the douche nozzle (presumably to avoid direct injection of irrigant into the natal woman's cervix), as is ideal for a neovagina in order to ensure that the blind-ending dome of the neovagina is thoroughly irrigated. Because prior art products are not designed for the unique anatomy of the neovagina, they often fail to provide sufficient hygiene and this can result in problems such as the formation of hypergrannulatuion at the dome of the neovagina, fluid discharge, infection, and discomfort.

Furthermore, another issue is that the current requirement to perform both dilation and douching is time-consuming and requires two separate devices. With increased complexity and time requirements, patient compliance rates are lower than optimal, resulting in complications.

Accordingly, there is a need in the art for improved neovaginal dilators which are comfortable, safe, effective, and more convenient. There is also a need in the art for improved neovaginal douching devices which improve the efficacy of irrigation of the neovagina.

There is also a need for neovaginal dilators which allow the patient to measure and track the depth of their neovagina over time, so that they can identify any loss of neovaginal depth and report this to their physicians. A neovaginal dilator that affords vaginal depth measurement is needed. Such a dilator is also useful for natal women who suffer from vaginal stenosis, were it is useful to assess vaginal depth at time of diagnosis, and/or to track vaginal depth over time in response to treatment.

Meanwhile, maintaining the health and function of the natal vagina may also be challenging in some individuals. In a related field, fertility is an issue for many couples, with impaired fecundity rates of 10% or more for some populations. In vitro fertilization provides a means of overcoming fertility problems for many couples, but is expensive, with average costs in the United States of US$>30,000, plus the cost of expensive medications. For couples with male-factor infertility (e.g. hypogonadism, where in the semen volume is abnormally low, or contains a low concentration of sperm, and/or for women who wish to become pregnant without having to have intercourse with a sperm donor, intravaginal insemination is a commonly offered option, wherein semen is introduced by a physician into the deepest portion of the vagina. This too, however, is quite expensive, and typically requires the services of a physician to introduce the semen into the vagina. A means by which an abundance of sperm could be introduced deep into the vagina, close to the optimal location near the cervix, would help couples whose infertility is caused by too few sperm per unit semen volume, or too low semen volume, and women who wish to forego intercourse in order to become pregnant. Such a device could also be used to introduce other medications to the vagina, as needed for vaginal health. Accordingly, there remains a need in the art for fertility aids and improved devices for maintaining the health and function of the natal vagina, and to improve fertility.

SUMMARY OF THE INVENTION

Disclosed herein are novel devices which improve the effectiveness, efficiency, and convenience of neovaginal maintenance. Various embodiments of the invention are also applicable in natal vaginal health maintenance and fertility applications, including novel douching devices, applicators for delivering therapeutic substances, and fertility aids.

In a first aspect, the scope of the invention is directed to a novel device with combined capabilities. The novel devices and associated methods of the invention are directed to the dilation and irrigation of the neo-vagina, as well as depth measurement of the neovagina. Advantageously, in one implementation, the invention provides the art with a combination device which allows for improved dilation, depth measurement, and, simultaneously, effective neo-vaginal douching. The combined "dilation-depth-douche" device ("DDD device") comprises a dilator with length markings starting at the tip that is inserted first into the neovagina, which can also act as a douche nozzle. This combination, and other features of the DDD, provide users with a greatly improved tool for neo-vaginal maintenance.

In another aspect, the devices of the invention provide medical professionals with tools for the creation of neovaginas and for assessing neovaginal depth and health.

In a third aspect, the scope of the invention encompasses novel devices for the delivery of agents or health-promoting stimuli to the neo or natal vagina. Delivered agents may include semen or isolated sperm, for insemination purposes.

BRIEF DESCRIPTION OF THE DRAWINGS

FIG. 1. FIG. 1 depicts an exemplary combination dilator and douche of the invention. The device comprises: a body (011); a base structure (002); an inlet port at the base, which can be a threaded connector for a standard douching bulb (005) the inlet in connection with an internal channel in the body, the position of which is denoted by dotted lines denoting an internal structure (009) and having lateral output ports (010) and an outlet port at the distal tip of the body (003); a contact point or indentation for receiving a vibrating device (006); in which one or more lateral outlet ports may (010) reside. The body comprise a gently curved S-shape, with opposing curved section at the distal (008) and proximal ends (007).

FIG. 2A, FIG. 2B, and FIG. 2C.

FIGS. 3A and 3B.

FIGS. 4A, 4B, and 4C.

FIGS. 5A and 5B.

DETAILED DESCRIPTION OF THE INVENTION

Neovaginal Dilator Devices. A first element of the dilator devices of the invention is the body. The body serves as a dilator. The body comprises an oblong tube, for example being circular or substantially circular in cross section. The body has a distal end, which is the end that is inserted deepest into the neo-vagina, and a proximal end, which remains outside the neo-vagina. The distal tip is blunted or rounded.

Figure 1:
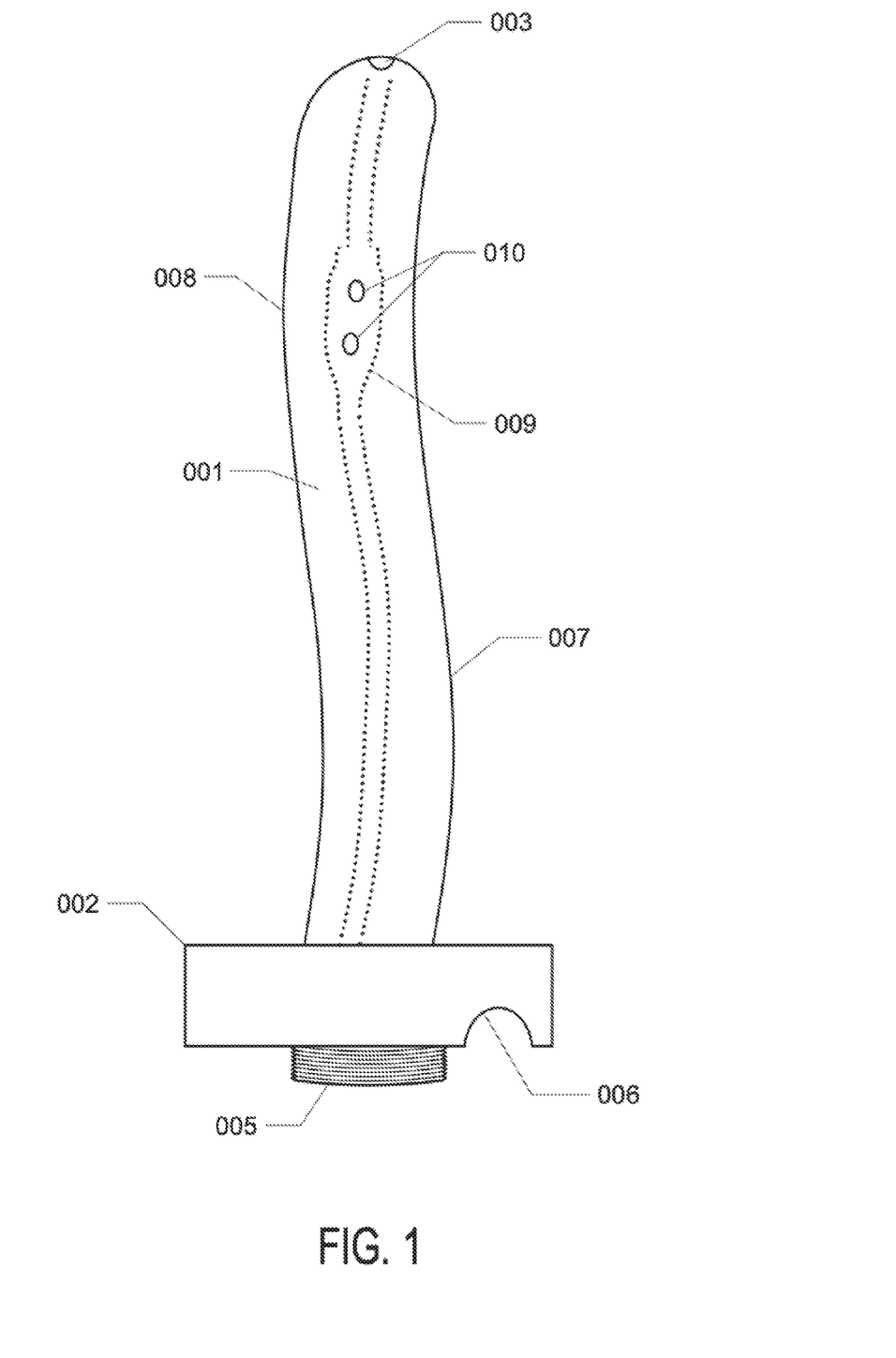
Figure 2A:
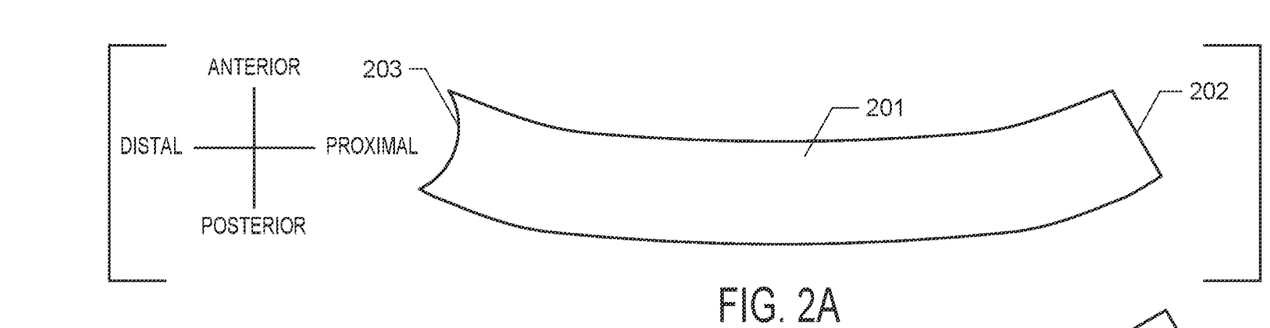
FIG. 2A depicts a common shape of the neovagina. The main channel (201) travels from the introitus (202) to the neovaginal dome (203).

In one embodiment, the body is tubular and straight. However, in preferred implementations, the body will comprise a shape that conforms to the anatomical shape or pathway of the typical neovagina. Based on extensive intraoperative and outpatient clinic observations by the inventor of the present disclosure, it has been determined that the neovagina assumes the shape of a flattened U, as in FIG. 2A. Typically, at the vaginal introitus, the first few centimeters of neovaginal tract point posteriorly, then the tract continues straight (parallel to the superior-inferior axis of the person) for a few centimeters, and over the last few centimeters of the neovaginal tract, its course becomes anteriorly oriented. Based on these anatomic investigations, the device of the invention may comprise a tubular body shaped to approximate the typical flattened U-shape or S-shape of the trajectory into a neovagina.

Figure 2B:
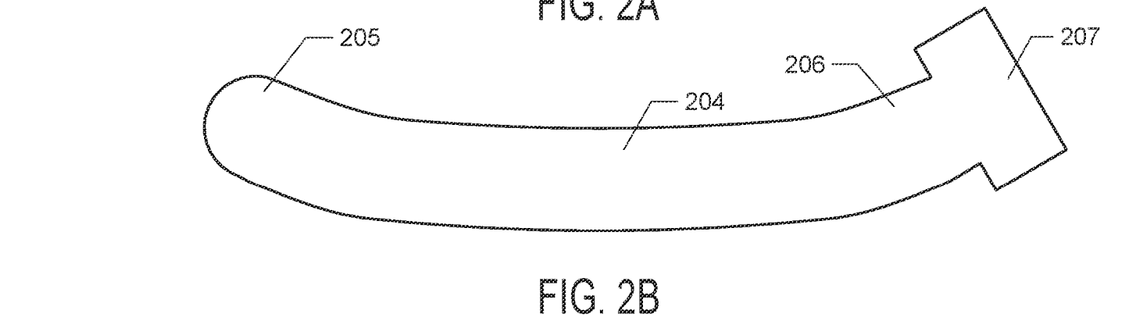
FIG. 2B depicts an exemplary U-shaped device for insertion into the neovagina, with a substantially straight intermediate section (204) flanked by gently curved proximal (206) and distal (205) sections pointed in the same direction, and a proximal base structure (207).

To accommodate the typical neovaginal geometry, the tubular body of the dilator device assumes the shape of a flattened U, with two gentle curves (for example, having 5-20 degrees of curvature from the long axis of the device) comprising the distal and proximal sections of the body. For example, each curve may comprise about 25-33% of the length of the body, as depicted in FIG. 2B. The intervening section may be straight or gently curved.

Figure 2C:
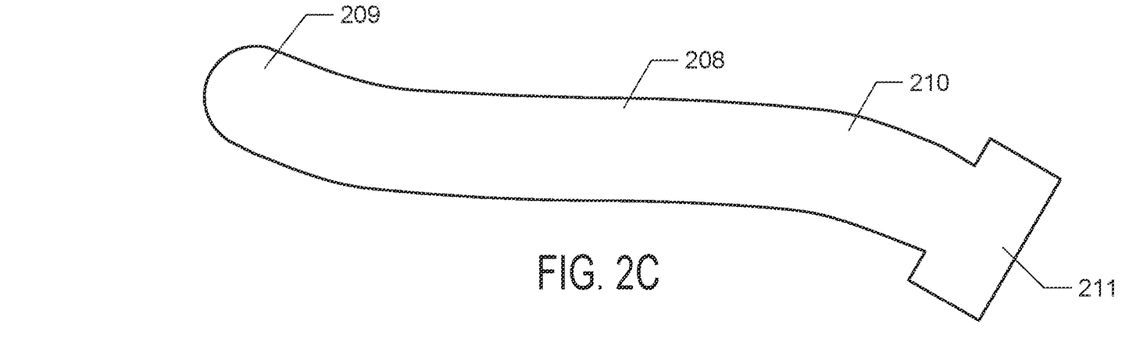
FIG. 2C depicts an exemplary S-shaped device for insertion into the neovagina, with a substantially straight intermediate section (208) flanked by gently curved proximal (210) and distal (209) sections curved in opposing directions, and a proximal base structure (211).

In an alternative embodiment, the body is generally S-shaped, comprising a distal curve (for example, having 5-20 degrees of curvature from the long axis of the device) and a proximal curve oriented in opposition (180 degrees) from the distal curve, for example as depicted in FIG. 2C. For example, each curve may comprise about 25-33% of the length of the body. The intervening section may be substantially straight or may comprise a sigmoidal inflection shape.

In contrast, the dilators of the prior art are largely straight, or, are made with a slight bend in the distal third of the body, such that upon insertion into the neo-vagina, the distal end of the dilator is pointing anteriorly (i.e. towards their anterior abdominal wall, instead of posteriorly towards their backside). The geometry of prior art neovaginal dilators does not reflect the typical trajectory of the neovagina and the use of such dilators is problematic as the lack of conformity to the trajectory of the neovagina creates pressure points which are painful or uncomfortable to the user and further which may damage or stress the tissues of the neovagina and surrounding organs.

The improved, anatomically compatible shape of the dilators of the invention provides users with a more comfortable, safe, and effective means of dilating the neovagina. The devices of the invention may be utilized in a method that prevents application of mechanical stress to the neovagina. In the method of the invention, the device is inserted with the distal tip initially pointing posteriorly, until a portion, for example about 4-10 cm, for example, about 6 cm, of the device has been inserted into the neovagina. A distance of 6 cm from the neovaginal introitus typically corresponds to the location of the prostate apex within the transgender woman's (genetically male) pelvis. The prostate Apex is the most posteriorly located solid structure located anteriorly along the neovaginal space. Upon reaching this point, the device is rotated 180-degrees, i.e. rotated such that the curved distal portion is pointed anteriorly—toward the sacral promontory. After rotation, the remainder of the device may be inserted.

To orient the user, the proximal end of the tubular body can be marked with a marking, for example, which is located such that it is visible only when the distal end of the device is pointing posteriorly. Alternatively, the 10 cm mark on the DDD shaft may be marked "Rotate 180°" to alert the user to rotate the device 180° when the 10 cm mark of the device reaches the neovaginal introitus. Upon rotating the device 180°, a second marking, for example, the letter "B," becomes visible on the proximal end of the dilator, and the distal-most end of the device will be pointing anteriorly. Importantly, in transgendered individuals, the rotation is performed after the distal-most end of the device is posterior to the base of the prostate gland, which avoids compression of the prostate or bladder. The dimensions of the proposed invention, having improved geometry and/or being flexible, can avoid the applied stresses that accompany use of prior art dilators.

The body may be provided in numerous lengths and diameters. Insertable length refers to the length of the device which can be inserted into the body. For example, an insertable body length of 10-20 cm, for example, may be utilized, to conform to the typical length of a neo-vagina. The body may be any diameter suitable for dilation of a neovagina, for example being 0.5 to 5 cm in diameter. Typically, patients with a new neovagina will commence dilation with a dilator of the largest diameter that is easily insertable (usually 2.5-3 cm), and then progress to progressively wider dilators (for example, in 0.3 cm diameter increments) over a period of days or weeks. Thus, the devices of the invention may be provided as a kit, the kit comprising two or more dilators of differing diameters, for example a kit of two or more, for example four, successively wider-diameter dilators having diameters ranging from 2.5 to 5 cm.

The proximal end of the body will preferably comprise a base structure to prevent over-insertion and also to aid in handling of the device. The base structure may comprise a flange, plate, or other structure that is substantially wider (e.g. 50-500% wider) than the diameter of the body. The base structure may comprise one or more grip features which allow the user to readily insert and move the device within the neovagina.

The body may comprise any suitable biocompatible material. In one implementation, rigid plastic is used to form the body, as in conventional dilators. In another implementation, the body may comprise semi-rigid, medical grade silicone. Other materials include PET, PVC, and latex. The use of semi-rigid materials allows for effective dilation with a more comfortable material having some flexibility, which allows the dilator to conform to the subtle shape asymmetry common to a space within the human body.

The outer surface of the body may be smooth, or may comprise various irregular features, shallow troughs, and protrusions, for example, having one or more ribbed or pebbled regions. These protrusion features advantageously increase stimulation (e.g. for promoting neuroplasticity, as discussed below) and may also help prevent the buildup of suction forces when the device is withdrawn. Smooth devices have been observed to stick to the surface of the neovagina, and the inclusion of surface features aids in promoting airflow to prevent such suction.

Ruler Markings. After vaginoplasty surgery, it is extremely important for the patient to dilate the entirety of the newly created neovaginal cavity. For this, the patient must know how deep to insert the dilator, in order to achieve safe dilation of the entire neovaginal cavity without over-inserting the dilator. For this, the surgeon must have a device with which to calibrate neovaginal depth at the time of surgery and the user must have a means of monitoring insertion depth.

Accordingly, the body of the dilator device may feature markings. For example, graduated length markings (beginning with zero at the distal tip) which delineate the distance from the distal tip can be used to monitor the depth of insertion. Such markings can be made on any single or multiple face(s) of the dilator device shaft, for example comprising circular rings circumscribing the body shaft. This allows the length markings to be visible to the user regardless of the rotated orientation of the dilator device during insertion.

Douching Function. The body of the dilator device can optionally act as a douching nozzle to introduce irrigant liquid to the full length of the neovagina. The body may comprise one or more internal channels, typically a single channel. The channel is a lumen with an inlet opening at the proximal end of the device, for example, located on the base structure. A connector or fitting present at the proximal end of the channel allows the channel to be connected to a source of irrigant for douching. The irrigant source will comprise a vessel for holding irrigant and a mechanism for expelling the irrigant from the vessel into the lumen of the dilator device. For example, the connector may comprise a Leuer-lock fitting or other syringe connector, so that a large irrigation syringe (e.g. 60 ml volume) can be connected to it, to serve as the douche reservoir, for manual irrigation of the douche irrigant through the dilator body. Alternatively, the distal inlet of the channel can be fitted with a threaded fitting, for compatibility with standard douche bulbs (typical capacity is approximately 250-350 cc. irrigant), which can be compressed to expel the irrigant. In other embodiments, the irrigant source is a combined reservoir and pump, for example, a battery-powered pump.

The outlet of the channel may comprise a single opening, or the channel may be branched and lead to multiple outlet ports along the body of the device. The one or more channel outlets may be located at the distal tip the dilator. In a preferred embodiment, there are a plurality of irrigant outlets, for example with one or more located at the distal tip of the device, and with one or more additional outlet ports along the length of the body, for example on two or more faces of the body, for lateral dispensation of irrigant.

In one implementation, the outlet may be configured and located such that the irrigant is not expelled directly at the vault, in order to reduce the risk of injury when this is a concern. For example, a curved channel with an outlet disposed to expel liquid proximally or at an angle may be used. Likewise, the terminal portion of the channel could branch and connect to multiple distal outlets, in order to dissipate the force of expelled irrigant.

The merged dilation and douching functionality of the combination device provides a significant improvement over prior art devices. Thorough irrigation of the neovagina is important, yet is hard to achieve with standard prior art douching devices which are designed for natal vaginas or the rectum. These standard douching devices have relatively short nozzles which are introduced into only the proximal region of the orifice. Short nozzles are effective in a natal vagina or in the rectum because the tissues thereof are naturally highly elastic and distensible, allowing them to be readily filled along their entire length with low pressure liquid. In contrast, neovaginal tissues are significantly less elastic. The distal end of the neovagina remains in a collapsed state and is less likely to become filled and distended with fluid using a standard device. A relatively high irrigation pressure is needed to distend the collapsed neo-vagina. Unless tented apart and washed by the douche irrigant, the distal-most end of the neo-vagina is not irrigated and cleansed by the irrigant solution. Stasis of pooled irrigant, lubricant, human fluids and shed debris from the skin typically results in chronic inflammation. This may likely contribute to the incidence of neovaginal bacterial overgrowth and/or the incidence of granulation tissue at the vault of the neovagina.

Because it is desirable that the force of the irrigant be greatest towards the end of the neovagina, in one implementation, the outlet ports are configured such that the net cross sectional area of the outlets through which the irrigant is expelled from the dilator device inside the neovagina is greatest for the hole(s) located on the end-face of the distal tip, as compared to the net cross sectional area of the holes located along the sides of the body of the device. This differential in irrigant-hole area (distal tip hole area being greater than area of holes along body-shaft) will result in the majority of the irrigant flowing through the distal tip of the device.

Using the novel combination devices of the invention, the elongated dilator body works as a douche nozzle wherein the liquid is introduced deeply in the neovagina. Advantageously, this allows tenting and effective irrigation of the distal portion thereof. Advantageously, the lumen of the combined device provides a conduit for air between the proximal and distal ends, which helps to prevent the buildup of suction forces in the neovagina when the device is withdrawn.

The body may further comprise one or more external troughs along its surface which extend from the distal tip to the proximal end. The function of the one or more troughs is to allow irrigant to backflow and drain along the body while it is firmly in place within the neo-vagina. The one or more drainage troughs may be linear. Alternatively, a spiraling drainage trough may be used in order to expose a greater proportion of the neovaginal wall to flowing irrigant. In a preferred embodiment, the floor of these troughs may possess small bumps ("speed-bumps") which cause any fluid flowing along the troughs to flow more turbulently. This is desirable because the less laminar and more turbulent the flow is, the more effective it will be in washing the walls of the neovagina free of debris (lubricant, bacteria, biofilms, etc.). An additional benefit of these troughs is that, by introducing an irregularity to the surface of the device, they lower the likelihood that a suction can be created between the device and the walls of the neovagina.

Low Intensity Vibration. A principal cause of adverse outcomes (scarring/shrinkage, skin necrosis) associated with construction of neovaginas is the lack of adequate blood supply. The portion of any free or pedicle skin-flap that is at highest risk of ischemia (lack of adequate blood flow necessary for tissue oxygenation and nutrition) is the portion of the flap furthest from the tissue's blood supply. This corresponds to the deepest (i.e. distalmost) portion of the neovaginal cavity which is furthest from the blood supply coming to the entire skin-tube from the inverted base of the skin-tube (i.e. from the base of the former penile shaft). It would therefore be desirable to apply treatments that promotes wound healing to the skin of the neovaginal wall and the surrounding neovagina vulva and neo-clitoris.

Research in other systems demonstrates that the application of low intensity vibrational energy promotes wound healing and angiogenesis. Accordingly, in one embodiment, the body of the device comprises a vibration-generating element, for example, located in the base structure of the device. In another embodiment, application of vibratory stimulation can be accomplished by applying a source of vibratory energy (e.g. a vibrator) to the proximal-most end of the device body, for example, to the body portion residing just-outside of the neovagina or to the base structure. The proximal end may comprise a recess that fits the end of a typical rounded-end vibrator, for example a concave cup-shaped recess or other contact point to which a second, vibrating device can be applied. During self-dilation, any generic vibrator can then be inserted into the recess to transmit vibratory energy along the dilator to the vestibule and interior or the neovagina.

For example, vibrations can be applied using apparatuses and treatment regimens known in the art for the application of therapeutic vibration, for example as described in Weinheimer-Haus et al., 2014, "Low intensity vibration improves angiogenesis and wound healing in diabetic mice," PLoS One 9(3):e91355; Arashi et al., 2010, "Vibration therapy accelerates healing of Stage 1 pressure ulcers in older adult patients," Adv Skin Wound Care 23: 321-7; and Shi et al., 2010, "Low-magnitude high-frequency vibration treatment augments fracture healing in ovariectomy-induced osteoporotic bone," Bone 46: 1299-1305. For example, in one embodiment, vibrations of 30-50 Hz are applied at times of 10 seconds to 30 minutes, with an amplitude modulation cycle of 15 seconds.

An additional novel use of vibrational stimulation is the promotion of neuroplasticity by activating sensory nerve pathways that map to the erogenous zones of the brain that previously received tactile and erogenous stimuli from the tip of the penis. Neuroplasticity is the brain's ability to reorganize itself by forming new neural connections throughout life, enabling neurons in the brain to compensate for injury and disease and to adjust their activities in response to new situations or to changes in their environment. For patients, promotion of neuroplasticity via application of vibrational stimuli via the device serves two important therapeutic purposes. First, activation of erogenous and tactile afferent sensory nerve pathways early after surgery helps establish a more permanent and robust sensory pathway to the brain between the newly formed neo-clitoris and the erogenous zone of the brain that used to map to the penis. Second, activation of erogenous and tactile afferent sensory nerve pathways emanating from the tissues of the neovaginal cavity and neoclitoris—especially when applied early after surgery helps the brain to re-map stimuli arising from the neoclitoris as corresponding to the patient's newly created vulva, as opposed to the previous location of the tip of the penis (i.e. several inches away from the pelvis).

In another embodiment, the device of the invention comprises a source of heat. Heat can aid in the healing process by stimulating blood flow. For example, internal heating elements, e.g. resistive wires, may be located within the tubular body, powered by a battery pack in the base structure.

Methods of Use. The scope of the invention encompasses dilators and combination dilator-douching devices having various combinations of the features set forth above. The scope of the invention further encompasses methods of using such devices for the simultaneous dilation and irrigation of the neo-vagina. The method of use for combination devices comprises the steps of (1) inserting the body of the device into the neo-vagina (for example, with rotation at about 10 cm, as described above); (2) leaving the dilator in place for a sufficient period to effect dilation, for example about twenty minutes; (3) connecting the base structure to a source of irrigant; and (4) actuating the irrigant source such that irrigant flows through the channel and exits from the one or more outlet ports located on the tubular body. Douching is typically performed after dilation is complete. Hence, with the devices of the invention, the douching activity could be performed by the user at the end of the dilation, simply by connecting the irrigant reservoir (e.g. douche bulb) to the to the device while the device remains in place within the neovagina—without the user needing to remove the dilator to replace it with a separate douche device.

In the method of the invention, vibratory energy may optionally be applied during the time the device is in place in the neovagina, if the device is configured to produce or transmit vibratory energy.

The irrigant may comprise tap-water, a saline solution, a therapeutic solution, etc. For example, approximately 200 to 400 ml of irrigant may be flowed into the neovagina during a douching process. In one embodiment, after rinsing the neovagina, the proximal end of the combination device can be connected to a source of warm low-pressure air to dry the deepest portion of the neovagina.

The combined dilator and douching apparatus of the invention provides various advantages to users. Dilation and douching are time consuming, for example with dilation being recommended for twenty minutes a day, 1-3 times per day, with mandatory douching afterwards to wash away lubricant used in inserting the dilator, such douching taking about 3-5 additional minutes. By allowing simultaneous dilation and douching, time is saved for the user and this may improve patient compliance. Additionally, the combined apparatus is more convenient as it halves the number of devices that the user must purchase and maintain. Additionally, by virtue of the combined apparatus already being inserted into the deep-most portion of the neovagina/vagina, it is ensured that the deepest portion of the neovagina is adequately exposed to the irrigant and will receive adequate irrigation with the douching solution, in contrast with typical douche devices which are shorter than the devices of the invention and thus typically introduce irrigant only to the proximal-most portion of the neovagina.

Medical Devices and Applications. The devices of the invention may also be configured and used to aid medical personnel in the creation of neovaginas, in assessing neovaginal health, and in therapeutic treatments.

In a first embodiment, the dilator device of the invention may comprise a surgical scaffold around which pieces of free skin are sutured together to form a skin-graft that will itself be sutured onto the more proximally-located pedicle skin flap. For example, during vaginoplasty, a U-shape or S-shaped body conforming the internal anatomy can be used as a scaffold-structure around which pieces of skin are sewn to each other, and, to skin harvested from the penis and already connected to the patient's body, to form the neovaginal channel. In one embodiment, the body of the surgical scaffold device comprises one or more holes, for example, in one embodiment, having holes around the entire surface of the body, into which disposable or re-usable pegs or other objects can be inserted and held in place. Skin or other tissues used to make the neovagina can be sutured to or otherwise affixed to such pegs and then placed into the complementary holes in order to hold skin or tissue sections in place while they are formed into a sheath and sutured together.

In another medical embodiment, markings, as described above, are utilized to evaluate the depth of the neovagina post-surgery so that patients can be informed of the proper depth of dilator insertion. Such measurement devices may also be used to monitor neovaginal depth over time so that closures due to scar tissue can be diagnosed.

The medical devices of the invention may comprise disposable or reusable devices. For example, if reusable, the device will comprise medical grade materials that can be autoclaved or otherwise sanitized to medical and operating room standards. Exemplary materials include medical grade plastics such as PVC, PET, latex, and silicone, or may comprise non-plastics such as ceramics, stainless steel, or titanium.

Dilators of different diameter can be colored differently, or, can be stamped with the specific dilator-diameter, so that patients readily know what diameter dilator they have been using, and, which is its approximate diameter.

Agent Delivery Devices. The scope of the invention further extends to devices for the delivery of agents to natal vaginas or neovaginas. In such embodiments, the device may comprise a body which conforms either to the shape of a natal vagina or to a neovagina; an internal channel, the proximal end of which may be connected to an agent source; and one or more outlets disposed along the body of the device from which agent is dispensed. In one embodiment, the device is designed for delivery of agents to the neovagina and is shaped to conform thereto (e.g. a flattened U-shaped or S-shaped device). The use of such devices is particularly advantageous for the delivery of agents to the neovagina because the channel must be distended or tented in order for agents to access the full length of the neovagina, and the tubular body provides a means of accessing the distal regions of the neovagina. In another embodiment, the device comprises a body designed to conform to the shape of a natal vagina, being substantially straight or gently curved.

The agent source may comprise, a syringe, a douche bulb, a pump and reservoir, or other vessel for liquid further comprising a mechanism to force the liquid into the internal channel of the device such that it is dispensed from the outlet port(s).

The substance to be dispensed may comprise a solution (e.g. saline) in which medically active substances are dissolved or suspended. For example, application of medicinal steroids and medicinal honey to a healing wound have been shown to accelerate healthy wound healing and to lower the incidence of hyper-granulation of tissue. Medicinal honey has also been shown to prevent bacterial colonization and infection and to improve the tensile strength of healing wound tissues. In another embodiment, the delivered substance may comprise a contrast agent or other imaging agent.

Fertility Aids. In one embodiment, the device of the invention comprises a fertility aid that deliverers sperm (as raw or processed semen) sperm to the cervical opening of the vagina of a natal woman. Such a device advantageously deposits an abundance of fresh semen or washed sperm all at once to the deepest portion of their vagina adjacent to the cervix, which can improve the probability of successful fertilization. Additionally, this device affords the collection of two or more ejaculates produced before female partner insemination to be collected, and inserted all at once, such a device provides a means of aiding couples and can be used privately at home, and avoids the expense of assisted reproductive technologies such as intravaginal and/or intrauterine insemination, or, IVF. Such devices may also appeal to surrogate mothers or women who otherwise do not wish to have intercourse with the sperm donor.

In such embodiments, the device may comprise a body which conforms to the shape of a natal vagina, being either straight or gently curved, an internal channel, the proximal end of which may be connected to a semen source; and one (or more) outlet at or near the distal end of the body, from which the semen is dispensed. The semen source may comprise a syringe, for example, which conforms to a complementary fitting located on the base of the device. The device may further comprise a base structure to prevent over-insertion and aid in handling. The length of the body may vary, for example from 10-20 cm and the width may vary as well for example, being in the range of 1-5 cm.

Figure 3A:
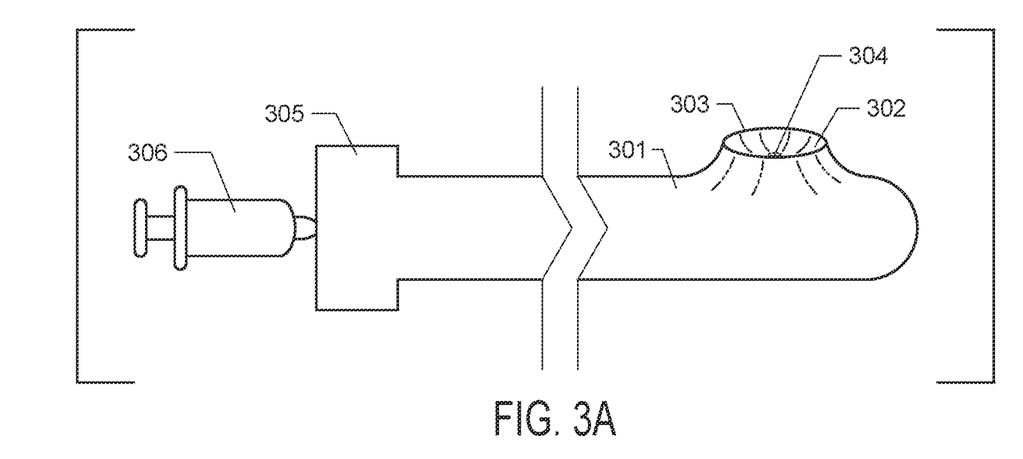
FIG. 3A depicts an exemplary insemination device for the delivery of semen to the cervical opening. The device comprises a body (301), and a distal cup (302) formed by a raised lip (303). Semen travels from a semen source, in this example a syringe (306) connected to the base structure (305), through an internal channel (not shown) an out of a distal output port (304) in the cup.
Figure 3B:
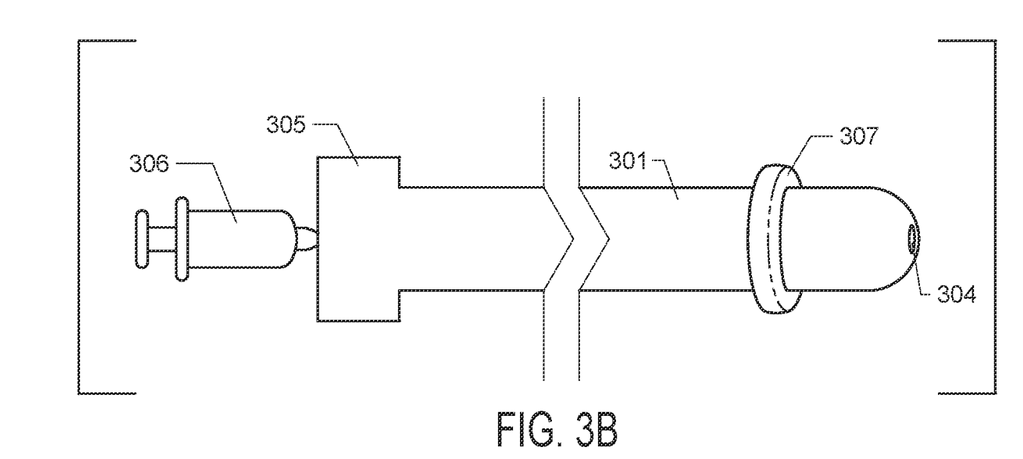
FIG. 3B depicts an agent delivery device for the neovagina or natal vagina, comprising a tubular body (301) having an internal channel (not shown), through which an agent can be flowed by connecting and actuating an agent delivery device (306) to one or more outlet ports on the body, for example (304), an outlet at the distal terminus. In this embodiment, the device comprises a collar (307) to prevent backflow of delivered agents, such as semen in the case of the device being used as an insemination device.
Figure 4A:
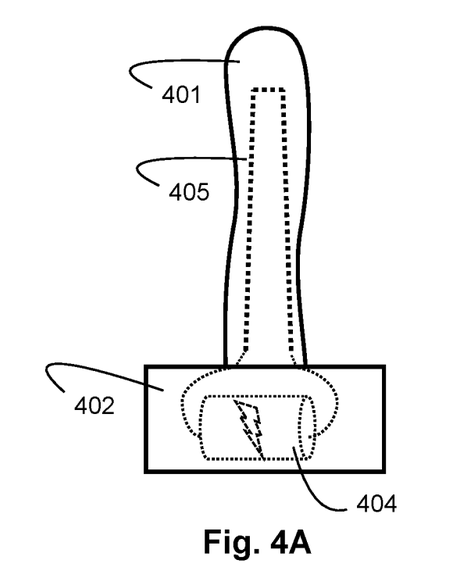
FIG. 4A depicts a device of the invention comprising a heat source. The device comprises a body (401) and a base (402). The heat source comprises a battery (404) housed in the base and internal resistive wires (405).
Figure 4B:
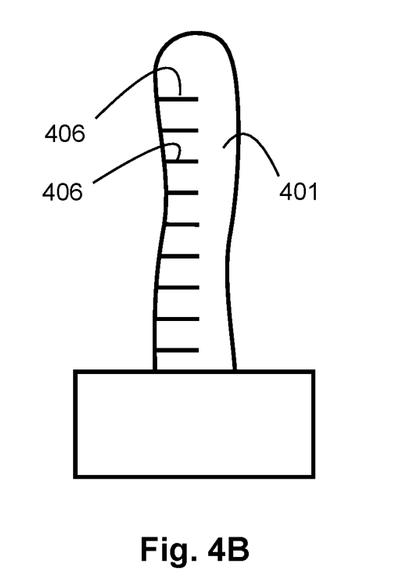
FIG. 4B depicts a device of the invention comprising a body (401) having a series of graduated ruler markings (406) to assist in determining depth of insertion.
Figure 4C:
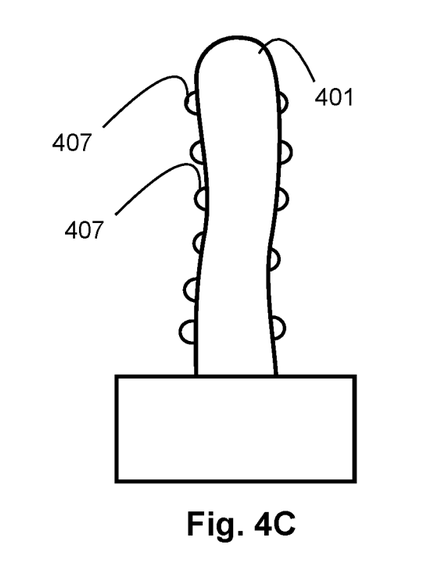
FIG. 4C depicts a device of the invention comprising a body, wherein the body a series of protrusions (407).
Figures 5A, 5B:
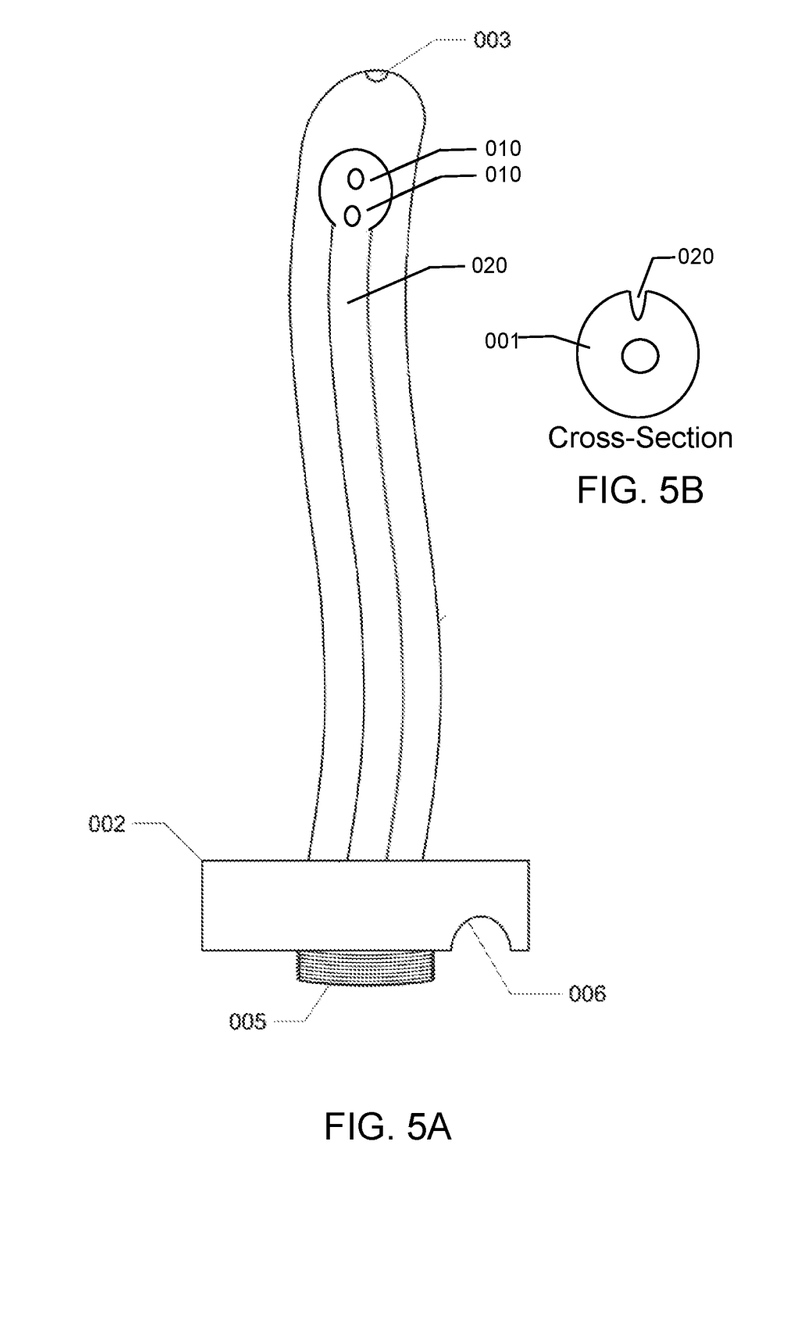
FIG. 5A depicts an exemplary combination dilator and douche of the invention comprising an external trough (020).
FIG. 5B depicts a cross section of the body depicted in FIG. 5A wherein the external trough (020) is evident.

The one or more outlet ports may be located at the distal tip of the device, or may be located 1-4 cm proximally of the distal tip, to align with the cervical opening, which is typically located somewhat proximal of the end of the natal vagina. The cervical opening is typically located either at the very end of the vaginal canal, or, on the anterior surface of the vagina close to the end of the end of the vaginal canal wall of the vagina, and the device may be configured with the outlet port(s) on one side of the body and a marking on the base structure or on the proximal end of the body that indicates the orientation of the outlet port[s] so that the user can align the port with the cervical opening. It is preferred that the internal channel be narrow (e.g. 0.25-2 mm in width) to avoid significant loss of semen from sticking to the channel walls. In one embodiment, the body comprises a collar, for example 2-10 mm in height, which surrounds the tubular body, is proximal to the semen outlet, and which acts as a barrier to prevent backflow of introduced semen. An exemplary insemination device comprising a collar is depicted in FIG. 3B. The collar may surround the tubular body in an annular manner (the radius of the collar being perpendicular to the long axis of the body, as in FIG. 3B, or the collar may be angled obliquely, i.e. off-center such that it assumes an elliptical ring.

In another embodiment, the end of the insemination device comprises a concave recession, surrounded by a lip or wall which extends from the surface of the body to create a cup-like structure. For example, the lip may protrude 2-10 mm from the body. This cup-shaped recession may be oriented perpendicular to the long axis of the body, parallel to the long axis of the body (wherein it forms the terminal end of the body), or at an intermediate angle, for example 30-60 degrees from the long axis of the body. The semen outlet will be in the center of the cup. The purpose of the cup-shaped recession is to pool the dispensed semen and keep it close to the target (just outside the cervix opening) and prevents backflow leakage of the delivered semen. An exemplary insemination device of this type is depicted in FIG. 3A. In an alternative embodiment, the annular ridge defining the depressed recess is oriented obliquely toward the tip, with the top of the ridge as depicted in 3A and the ventral end of ridge is located just below the tip of the dilator, such that the entire dorsal surface of the tip of the dilator lies within the recess, while the ventral surface of the dilator end lies outside of the depressed area.

The insemination device may comprise a source of vibration, or may comprise a concave groove or other structure at the base of the device which enables application of a vibrational energy source to the device.

A method of using the insemination device encompasses: collection of semen and its placement in the semen delivery source (e.g. syringe); insertion of the body of the insemination device into the vagina; connection of the semen source to the coupling at the proximal end of the insemination device; actuation of the semen source (e.g. depressing the syringe) to force semen through the internal channel such that it is expelled at or near the cervical opening; and optionally, keeping the device inserted for a time period (e.g. 5-20 minutes) to prevent semen escape from the cervical region.

During the use of the inseminator, vibration may be applied purpose of activating the all-natural cascade of fertilization-promoting spasms/reflexes that the female reproductive tract enacts during copulation to optimize the likelihood that intercourse will lead to fertilization (e.g. the vagina, cervix and uterus spasm during orgasm, which is believed to help draw sperm past the cervix and into the uterus).

All patents, patent applications, and publications cited in this specification are herein incorporated by reference in their entirety to the same extent as if each independent patent, patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A neovaginal dilator, comprising
a tubular body having a distal and proximal end,
wherein the distal end is blunted or rounded;
wherein the proximal end is connected to a base structure; and
wherein the body is shaped to conform to a neovagina and is configured for insertion therein,
the body comprising:
a curved distal section comprising 25-33% of the length of the body;
a curved proximal section comprising 25-33% of the length of the body; and
a substantially straight intervening section dispose between the distal curved section and the proximal curved section.

2. The neovaginal dilator of claim 1, wherein
the curved proximal section and curved distal sections are angled in the same direction.

3. The neovaginal dilator of claim 1, wherein
the curved proximal section and curved distal sections are angled in opposing directions.

4. The neovaginal dilator of claim 1, wherein
the dilator also comprises a douching nozzle;
wherein the tubular body comprises an internal channel,
wherein the proximal end of the channel is located in the base structure and comprises a fitting for an irrigant source; and
wherein the channel comprises one or more outlets on tubular body.

5. The neovaginal dilator of claim 4, wherein
the fitting comprises a Leuer lock or a threaded or a locking connection for a douche bulb.

6. The neovaginal dilator of claim 4, wherein
the outer surface of the body comprises one or more external troughs.

7. The neovaginal dilator of claim 4, wherein
the outer surface of the tubular body comprises a plurality of protrusions.

8. The neovaginal dilator of claim 1, further comprising
a series of markings along the length of the tubular body that indicate the distance from the distal end of the tubular body.

9. The neovaginal dilator of claim 1, further comprising
a source of vibrational energy or a contact point for transmission of vibrational energy from another device.

10. The neovaginal dilator of claim 1, further comprising
a source of heat.

11. A method of inserting a neovaginal dilator,
wherein the neovaginal dilator comprises a tubular body having a distal and proximal end and wherein the distal and proximal ends of the tubular body are curved, the method comprising the steps of:
inserting the distal tip of the tubular body into the neovaginal introitus, wherein the curved distal portion is oriented posteriorly, to a depth of about 6 cm;
rotating the tubular body 180 degrees; and
continuing to insert the tubular body until it substantially fills the neovagina.

12. A device for delivering agents to a neovagina or natal vagina comprising
a tubular body having a distal end and a proximal end;
wherein the tubular body comprises an internal channel, wherein the proximal end of the channel comprises a fitting for connection with a source of agent;
wherein the distal end of the internal channel comprises an output port; and
wherein the distal end of the tubular body comprises a concave recession,
wherein the outlet port is in the concave recession.

13. The device for delivering agents to a neovagina or natal vagina of claim 12, further comprising
a source of vibrational energy located in a base structure present at the proximal end of the body or a contact point for applying vibrational energy from a separate vibrating device.

14. The device for delivering agents to a neovagina or natal vagina of claim 12, wherein
the outlet ports is located at the distal tip of the device, or is located 1-4 cm proximally of the distal tip.

15. A device for delivering agents to a neovagina or natal vagina comprising
a tubular body having a distal end and a proximal end;
wherein the tubular body comprises an internal channel, wherein the proximal end of the channel comprises a fitting for an agent delivery device;
wherein the distal end of the internal channel comprises one or more output ports; and
wherein the tubular body comprises a collar, which surrounds the tubular body, and which is located proximal to the one or more outlet ports.

16. The device for delivering agents to a neovagina or natal vagina of claim 12, wherein
the base or the proximal end of the tubular body comprises markings that enable the user to align the one or more outlet ports with the cervix.

17. The device for delivering agents to a neovagina or natal vagina of claim 12, wherein
the proximal end of the tubular body comprises an agent delivery device comprising a source of semen.

18. The device for delivering agents to a neovagina or natal vagina of claim 15, further comprising
a source of vibrational energy located in the base structure or a contact point for applying vibrational energy from a separate vibrating device.

19. The device for delivering agents to a neovagina or natal vagina of claim 15, wherein
the one or more outlet ports is located at the distal tip of the device, or is located 1-4 cm proximally of the distal tip.

20. The device for delivering agents to a neovagina or natal vagina of claim 15, wherein
the base or the proximal end of the tubular body comprises markings that enable the user to align the one or more outlet ports with the cervix.

21. The device for delivering agents to a neovagina or natal vagina of claim 15, wherein
the proximal end of the tubular body comprises an agent delivery device comprising a source of semen.

* * * * *